US008512706B2

(12) United States Patent
López De Silanes et al.

(10) Patent No.: US 8,512,706 B2
(45) Date of Patent: Aug. 20, 2013

(54) COMPOSITIONS OF F(AB')₂ ANTIBODY FRAGMENTS

(75) Inventors: Juan López De Silanes, México City (MX); Rita Guadalupe Mancilla Nava, México City (MX); Jorge F. Paniagua-Solís, México City (MX); Alejandro Alagon Cano, Cuernavaca (MX); Walter J. García-Ubbelohde, México City (MX)

(73) Assignee: Instituto Bioclon, S.A. DE C.V., Mexico City (MX)

( * ) Notice: Subject to any disclaimer, the term of this patent is extended or adjusted under 35 U.S.C. 154(b) by 0 days.

(21) Appl. No.: 13/298,778

(22) Filed: Nov. 17, 2011

(65) Prior Publication Data

US 2012/0064063 A1    Mar. 15, 2012

Related U.S. Application Data

(62) Division of application No. 12/326,687, filed on Dec. 2, 2008, now Pat. No. 8,075,893, which is a division of application No. 10/690,639, filed on Oct. 23, 2003, now Pat. No. 7,485,303, which is a division of application No. 09/798,076, filed on Mar. 5, 2001, now Pat. No. 6,709,655.

(51) Int. Cl.
    *A61K 39/395* (2006.01)
(52) U.S. Cl.
    USPC .................. 424/158.1; 424/133.1; 424/177.1; 424/185.1
(58) Field of Classification Search
    None
    See application file for complete search history.

(56) References Cited

U.S. PATENT DOCUMENTS

| | | |
|---|---|---|
| 4,401,663 A | 8/1983 | Buckwalter et al. |
| 4,806,346 A | 2/1989 | Hum et al. |
| 4,814,433 A | 3/1989 | Fredrickson |
| 4,849,352 A | 7/1989 | Sullivan et al. |
| 4,940,670 A | 7/1990 | Rhodes |
| 5,328,834 A | 7/1994 | Ngo et al. |
| 5,443,976 A | 8/1995 | Carroll |
| 5,733,742 A | 3/1998 | Landon |
| 5,888,511 A | 3/1999 | Skurkovich et al. |
| 5,904,922 A | 5/1999 | Carroll |
| 6,270,766 B1 | 8/2001 | Feldman et al. |
| 6,333,032 B1 | 12/2001 | Skurkovich et al. |
| 6,448,054 B1 | 9/2002 | Poznansky et al. |
| 6,534,059 B2 | 3/2003 | Skurkovich et al. |
| 6,709,655 B2 | 3/2004 | López de Silanes et al. |
| 6,861,056 B2 | 3/2005 | Skurkovich et al. |
| 7,232,568 B2 | 6/2007 | Skurkovich et al. |
| 7,250,165 B2 | 7/2007 | Heavner et al. |
| 7,381,802 B2 | 6/2008 | López de Silanes et al. |
| 7,485,303 B2 | 2/2009 | López de Silanes et al. |
| 8,075,893 B2 | 12/2011 | LóPez de Silanes et al. |
| 2001/0021380 A1 | 9/2001 | Pluenneke |
| 2003/0049725 A1 | 3/2003 | Heavner et al. |
| 2003/0180294 A1 | 9/2003 | DeVries |
| 2003/0215448 A1 | 11/2003 | Skurkovich et al. |
| 2003/0223995 A1 | 12/2003 | Skurkovich et al. |
| 2003/0224005 A1 | 12/2003 | Skurkovich et al. |
| 2003/0228310 A1 | 12/2003 | Skurkovich et al. |
| 2004/0062768 A1 | 4/2004 | Skurkovich et al. |
| 2004/0086508 A1 | 5/2004 | Skurkovich et al. |
| 2006/0210563 A1 | 9/2006 | López de Silanes et al. |

FOREIGN PATENT DOCUMENTS

| | | |
|---|---|---|
| AU | 2002237586 B2 | 9/2002 |
| EP | 0 068 592 B1 | 1/1983 |
| EP | 0 089 710 B1 | 9/1983 |
| EP | 0 492 448 A1 | 7/1992 |
| EP | 0 516 785 B1 | 2/1996 |
| EP | 1 035 209 A1 | 9/2000 |
| ES | 2 106 183 | 11/1997 |
| WO | WO 92/22324 | 12/1992 |
| WO | WO 00/27421 A2 | 5/2000 |
| WO | WO 00/53786 A1 | 9/2000 |
| WO | WO 01/58469 | 8/2001 |
| WO | WO 02/068475 A2 | 9/2002 |
| WO | WO 2005/009464 A1 | 2/2005 |

OTHER PUBLICATIONS

Cain, B.S., et al., "The Physiologic Basis for Anticytokine Clinical Trials in the Treatment of Sepsis," *J. Am. Coll. Surg.* 186:337-351, American College of Surgeons (1998).
Fekade, D., et al., "Prevention of Jarisch-Herxheimer Reactions by Treatment with Antibodies Against Tumor Necrosis Factor α," *N. Engl. J. Med.* 335:311-315, Massachusetts Medical Society (1996).
Fox, D.A., "Cytokine Blockade as a New Strategy to Treat Rheumatoid Arthritis," *Arch. Intern. Med.* 160:437-444, American Medical Association (2000).
Krueger, J.G., "The Immunologic basis for the treatment of psoriasis with new biologic agents," *J. Am. Acad. Dermatol.* 46:1-23, Mosby (2002).
Lisman, K.A., et al., "Managing Heart Failure with Immunomodulatory Agents," *Cardiol. Clin.* 19:617-625, W.B. Saunders Co. (2001).
Luger, T., "Treatment of immune-mediated skin disease: future perspectives," *Eur. J. Dermatol.* 11:343-347 , John Libbey Eurotext (2003), downloaded from: http://www.john-libbey-eurotext.fr/en/revues/medecine/eid/e-docs/00/01/88/A6/article.md.
Martin, G.S., "Current Management Strategies for Severe Sepsis and Septic Shock," Presented at Chest 2001: 67th Annual Scientific Assembly of the American College of Chest Physicians, Nov. 4-8, 2001, Philadelphia, PA, downloaded from: http://www.medscape.com/viewarticle/412927.

(Continued)

*Primary Examiner* — Yunsoo Kim
(74) *Attorney, Agent, or Firm* — Sterne, Kessler, Goldstein & Fox P.L.L.C.

(57) ABSTRACT

The present invention is directed to a pharmaceutical composition comprising F(ab')₂ antibody fragments that are preferably free from albumin and of whole antibodies and also substantially free of pyrogens, and an effective amount of a pharmaceutically acceptable carrier. It is also directed to a method for the production of a pharmaceutical composition comprising F(ab')₂ antibody fragments using scrum or blood plasma of a mammal that has been previously immunized as a source of antibodies. The serum or blood plasma is digested with an enzyme pepsin, followed by separation and purification until the pharmaceutical composition of F(ab')₂ fragments is free of albumin and complete antibodies, and substantially free of pyrogens.

15 Claims, 8 Drawing Sheets

(56) References Cited

OTHER PUBLICATIONS

Figure 1:
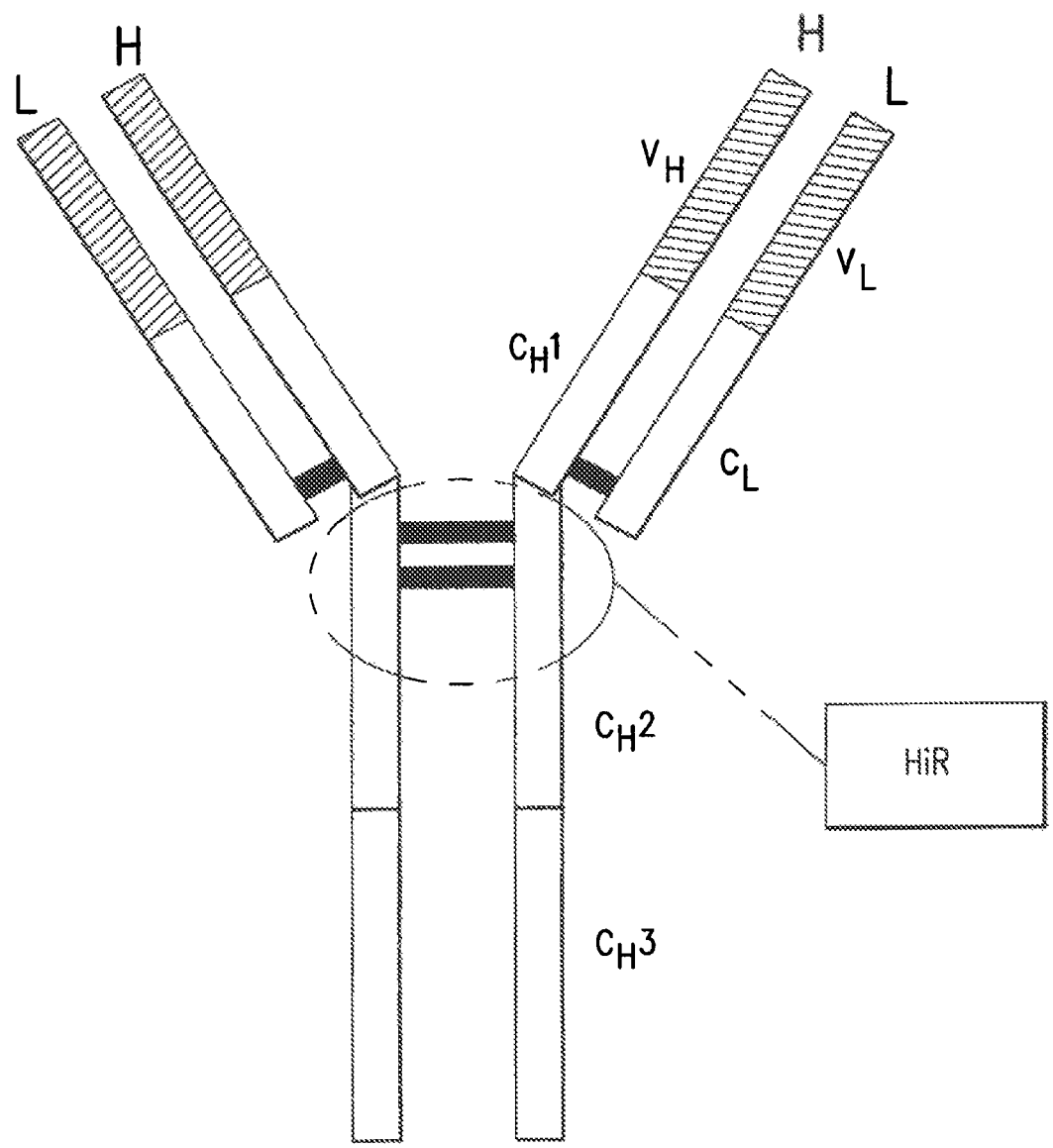

Present, D.H., et al., "Infliximab for the Treatment of Fistulas in Patients with Crohn's Disease," *N. Engl. J. Med.* 340:1398-1405, Massachusetts Medical Society (1999).

Qian, Y., et al., "Topical Soluble Tumor Necrosis Factor Receptor Type I Suppresses Ocular Chemokine Gene Expression and Rejection of Allogenic Corneal Transplants," *Arch. Ophthalmol.* 118:1666-1671, American Medical Association (2000).

Stapczynski, J.S., "Shock, Septic," Dire, D.J., et al., eds., eMedicine.com Inc., (2004), downloaded from: http://emedicine.com/EMERG/topic533.htm.

Torres, P.F., and Kijlstra, A., "The role of cytokines in corneal immunopathology," *Ocul. Immunol. Inflamm.* 9:9-24, Swets & Zeitlinger (2001).

Zhu, S., et al., "Early Expression of Proinflammatory Cytokines Interleukin-1 and Tumor Necrosis Factor-α after Corneal Transplantation," *J. Interferon. Cytokine. Res.* 19:661-669, Mary Ann Liebert, Inc. (1999).

Abstract of Dick, A.D., et al., "Neutralizing TNF-α Activity Modulates T-cell Phenotype and Function in Experimental Autoimmune Uveoretinitis," *J. Autoimmun.* 11:255-264, Academic Press (1998), downloaded from: http://80-www.elsevier.com.proxygw.wrlc.org/wps/find/journaldescription.cws_home/622856/description.

International Search Report for International Patent Application No. PCT/MX02/0013, mailed Aug. 16, 2002.

Dialog File 351, Accession No. 9271133, Derwent WPI English language abstract for Spanish Patent No. 2 106 183 (Document FP1), 2002.

English language translation of Secretaría de Salud, "Potency of Anti-Poison Sera," in *Farmacopea de los Estados Unidos Mexicanos*, vol. II, Secretaría de Salud, Mexico City, MX, pp. 1756-1757 (2000).

English language translation of Secretaría de Salud, "Pyrogen Tests," in: *Farmacopea de los Estados Unidos Mexicanos*, vol. I, Secretaría de Salud, Mexico City, MX, pp. 334-335 (2000).

Calderon-Aranda, E.S., et al., "Neutralizing capacity of murine sera induced by different antigens of scorpion venom," *Toxicon* 31:327-337, Pergamon Press Ltd. (1993).

Licea, A.F., et al., "FAB fragments of the monoclonal antibody BCF2 are capable of neutralizing the whole venom from the scorpion *Centruroides noxius* hoffman," *Toxicon* 34:843-847, Pergamon Press Ltd. (1996).

Banks, N., "Synopses of North-American Invertebrates. IX. The Scorpions, Solpugids, and Pepipalpi," *Am. Nat.* 34:421-427, Ginn & Company, Publishers (1900).

Banks, N., "The Scorpions of California," *Pomona College J. Entomol.* 2:185-190, The Biological Department of Pomona College (1910).

Barona, J., et al., "Aspectos toxinológocos e immunoquímicos del veneno del scorpion *Tityus pachyurus* Pocock de Colombia: capacidad neutralizante de antivenenos producidos en Latino américa, or in English: Toxicological and immunological aspects of scorpion poison (*Tytius pachyurus*): neutralizing capacity of antipoisons produced in Latin America," *Biomédica* 24:42-49, Instituto Nacional de Salud (Mar. 2004).

Unverified English language translation of Barona, J., et al., "Toxicological and immunological aspects of scorpion poison (*Tytius pachyurus*): neutralizing capacity of antipoisons produced in Latin America," *Biomédica* 24:42-49, Instituto Nacional de Salud (Mar. 2004).

Becerril, B., et al., "Cloning and characterization of cDNAs that code for Na$^+$-channel-blocking toxins of the scorpion *Centruroides noxius* Hoffman," *Gene* 128:165-171, Elsevier Science Publishers B.V. (1993).

Calderon-Aranda, E.S., et al., "The use of synthetic peptides can be a misleading approach to generate vaccines against scorpion toxins," *Vaccine* 13:1198-1206, Elsevier Science, Ltd. (1995).

Couraud, F., et al., "Two Types of Scorpion Toxin Receptor Sites, One Related to the Activation, the Other to the Inactivation of the Action Potential Sodium Channel," *Toxicon* 20:9-16, Pergamon Press, Ltd. (1982).

Curry, S.C., et al., "Envenomation by the Scorpion Centruroides Sculturatus," *J. Toxicol.-Clin. Toxicol.* 21:417-449, Marcel Dekker, Inc. (1983-1984).

Dehesa-Davila, M. and Possani, L.D., "Scorpionism and Serotherapy in Mexico," *Toxicon* 32:1015-1018, Elsevier Science, LTD. (1994).

Dehesa-Davila, M., et al., "Clinical Toxicology of Scorpion Stings," in *Handbook of Clinical Toxicology of Animal Venoms and Poisons*, Meier, J. and White, J., eds., CRC Press, Boca Raton, LA, pp. 221-238 (1995).

Diaz Najera, A., "Alacranes de la Republica Mexicana: Identificación de ejemplares capturados en 235 localidades," *Rev. Inst. Salubr. Enferm. Trop.* (Méx) 24:15-30, Instituto de Salubridad y Enfermedades Tropicales (1964).

Edman, P. and Begg, G., "A Protein Sequenator," *European J. Biochem.* 1:80-91, Blackwell Science, Ltd. on behalf of the Federation of European Biochemical Societies (1967).

Ewing, H.E., "The Scorpions of the Western Part of the United States, with Notes on Those Occuring in Northern Mexico," *Proc. U.S. Natl. Mus.* 73:1-24, United States Government Printing Office (1928).

Garcia, C., et al., "Isolation, Characterization and Comparison of Novel Crustacean Toxin with a Mammalian Toxin from the Venom of the Scorpion *Centruroides noxius* Hoffman," *Comp. Biochem. Physiol.* 116B:315-322, Elsevier Science, Inc. (1997).

Gertsch, W.J., "Results of the Puritan-American Museum Expedition to Western Mexico 4. The Scorpions," *Am. Mus. Novitates*, No. 1903, pp. 1-20, The American Museum of Natural History (1958).

Hoffman, C.C., "Monografias para la Entomologica Medica de Mexico, Los Scorpiones de Mexico," in: *Anales del Instituto de Biologica*, Ochoterena, I., ed., Universidad Nacional Autonoma de Mexico, Mexico, pp. 243-361 (1932).

Johnson, J.D. and Allred, D.M., "Scorpions of Utah," *Great Basin Nat.* 32:154-170, M.L. Bean Life Science Museum (1972).

Legros, C., et al., "Use of fusion protein constructs to generate potent immunotherapy and protection against scorpion toxins," *Vaccine* 20:934-942, Elsevier Science, Ltd. (Dec. 2002).

Maraboto Martinez, J.A., et al., "Panorama Epidemiológico de las Intoxicaciones Causadas por Animales Ponzoñosos en la Población Derechohabiente del IMSS 1990-1998," in *3ªReunión de Expertos en Envenenamiento por Animales Ponzoñosos*, Instituto de Biotecnología, Universidad Nacional Autónoma de México, Alcapulco, Gro., México (1999).

English translation of Maraboto Martinez, J.A., et al., "Intoxications Caused by Poisonous Animals among IMSS Right-Holders, 1990-1998. An Epidemiological overview," in *3ªReunión de Expertos en Envenenamiento por Animales Ponzoñosos*, Instituto de Biotecnología, Universidad Nacional Autónoma de México, Alcapulco, Gro., México pp. 1-14 (1999), translated by Amador Rodriquez, J.C. (Dec. 2004).

Meeting regarding additional remarks by Dr. Marx on Aug. 4, 1887, *Proc. Entomol. Soc.* 1:90-94, The Entomological Society (1884-1889).

Nonner, W., "Effects of *Leiurus* Scorpion Venom on the "Gating" Current in Myelinated Nerve," *Adv. Cytopharmacol.* 3:345-352. Raven Press (1979).

Possani, L.D., et al., "Scorpion toxins from *Centruroides noxius* and *Tityus serrulatus*," *Biochem. J.* 229:739-750, Biochemical Society/Portland Press (1985).

Possani, L.D., et al., "Scorpion toxins specific for NA$^+$ -channels," *Eur. J. Biochem.* 264:287-300, Blackwell Science, Ltd. on behalf of the Federation of European Biochemical Societies (1999).

Possani, L.D., et al., "Peptides and genes coding for scorpion toxins that affect ion-channels," *Biochimie* 82:861-868, Editions Scientifiques Elsevier (2000).

Stahnke, H.L., "The Scorpions of Arizona," *J. Sci.* (*Iowa State College*) 15:101-103, Collegiate Press, Inc. (1940-1941).

Stahnke, H.L., "Some Observations of the Genus Centruroides Marx (Buthidae Scorpionida) and C. Sculpturatus Ewing," *Ent. News* 82:281-307, The American Entromological Society (1971).

Strichartz, G., et al., "An Integrated View of the Molecular Toxinology of Sodium Channel Gating in Excitable Cells," *Ann. Rev. Neurosci.* 10:237-267, Annual Reviews, Inc. (1987).

Suchard, J.R. and Connor, D.A., "Scorpion Envenomation," in: *Wilderness Medicine*, Auerbach, P.S., ed., Mosby, St. Louis, MO, pp. 839-862 (Feb. 2001).

Williams, S.C. and Hadley, N.F., "Scorpions of the Puerto Peñasco Area (Cholla Bay), Sonora, Mexico, with Description of *Vejovis baergi*, New Species," *Proc. California Acad Sci. 35*:103-116, California Academy of Sciences (1967).

Williams, S.C., "Scorpions of Baja California, Mexico, and Adjacent Islands," *Occasional Papers of the California Academy of Sciences*, No. 135, pp. 1-127, California Academy of Sciences (1980).

Wood, H.C., Jr., "Description of New Species of North American Pedipalpi," *Proc. Acad. Natl. Sci. Philadelphia 15*:107-112, Merrihew & Thompson (1863).

Wood, H.C., Jr., "Art. VII. On the Pedipalpi of North America," *J. Acad. Natl. Sci. Philadelphia 5*:357-376, Merrihew & Thompson (1862-1863).

Zamudio, F., et al., "Amino acid sequence and immunological characterization with monoclonal antibodies of two toxins from the venom of the scorpion *Centruroides noxius* Hoffman," *Eur. J. Biochem. 204*:281-292, Blackwell Science, Ltd. on behalf of the Federation of European Biochemical Societies (1992).

Zlotkin, E. and Strilov, A.S., "Recent Studies on the Mode of Action of Scorpion Neurotoxins. A Review," *Toxicon 7*:217-221, Pergamon Press (1969).

Zlotkin, E., et al., "C. Chemistry and Pharmacology of Buthinae Scorpion Venoms," in: *Arthropod Venoms*, Bettini, S., ed., Springer-Verlag, Berlin, Germany, pp. 317-369 (1978).

Burton, D.R., et al., "HIV vaccine design and the neutralizing antibody problem," *Nat. Immunol. 5*:233-236, Nature Publishing Group (Mar. 2004).

Calderon-Aranda, E.S., et al., "Pharmacokinetics of the toxic fraction of Centruroides limpidus limpidus venom in experimentally envenomed rabbits and effects of immunotherapy with specific F(ab')$_2$," *Toxicon 37*:771-782, Pergamon Press (1999).

Campbell, A.M., *Monoclonal Antibody and Immunosensor Technology*, Elsevier Science Ltd., vol. 23, pp. 288-291 (1991).

Harlow, E. and Lane, D., *Antibodies: A Laboratory Manual*, Cold Spring Harbor Laboratory Press, Cold Spring Harbor, New York, pp. 298-299 (1988).

Vanlandschoot, P., et al., "An antibody which binds to the membrane-proximal end of influenza virus haemagglutinin (H3 subtype) inhibits the low-pH-induced conformational change and cell-cell fusion but does not neutralize virus," *J. Gen. Virol. 79*:1781-1791, Socity For General Microbiology (1998).

Hoffmann, E., et al., "A DNA transfection system for generation of influenza A virus from eight plasmids," *Proc. Natl. Acad. Sci. USA 97*:6108-6113, National Academy of Sciences, United States (May 2000).

Hoffmann, E., et al., "'Ambisense' Approach for the Generation of Influenza A Virus: vRNA and mRNA Synthesis from One Template," *Virol. 267*:310-317, Academic Press, United States (Feb. 2000).

Neumann, G., et al., "Plasmid-Driven Formation of Influenza Virus-Like Particles," *J. Virol. 74*:547-551, American Society for Microbiology, United States (Jan. 2000).

International Search Report for International Application No. PCT/IB03/02971, mailed Jun. 2, 2004, ISA/US, United States.

Office Action mailed Apr. 1, 2003 for U.S. Appl. No. 09/798,076, filed Mar. 5, 2001.

Office Action mailed Sep. 10, 2002 for U.S. Appl. No. 09/798,076, filed Mar. 5, 2001.

Office Action mailed Sep. 15, 2008 for U.S. Appl. No. 10/565,885, § 371(c) date: Jan. 25, 2006.

Office Action mailed Dec. 15, 2006 for U.S. Appl. No. 10/690,639, filed Oct. 23, 2003.

Office Action mailed Apr. 11, 2008 for U.S. Appl. No. 10/690,639, filed Oct. 23, 2003.

Office Action mailed Mar. 21, 2006 for U.S. Appl. No. 10/690,639, filed Oct. 23, 2003.

Jain, R.K., "Vascular and interstitial barriers to delivery of therapeutic agents in tumors," *Cancer Metastasis Rev. 9*:253-266, Kluwer Academic Publishers, Netherlands (1990).

Jain, R.K., "Transport of Molecules, Particles, and Cells in Solid Tumors," *Annu. Rev. Biomed. Eng. 1*:241-263, Annual Reviews, United States (1999).

Looareesuwan, S., et al., "Polyclonal Anti-Tumor Necrosis Factor-α Fab Used as an Ancillary Treatment for Severe Malaria," *Am. J. Trop. Med. Hyg. 61*:26-33, The American Society of Tropical Medicine and Hygiene, United States (1999).

Merck Manual of Diagnosis and Therapy (Mark Beers and Robert Berkow eds.), Published by Merck Research Laboratories, United States, 17$^{th}$ ed., pp. 722-724 (1999).

Sasaki, H., et al., "Enhancement of Ocular Drug Penetration," *Crit. Rev. Ther. Drug Carrier Syst. 16*:85-146, Begell House, Inc., United States (1999).

Tannock, I.F., "Tumor physiology and drug resistance," *Cancer Metastasis Rev. 20*:123-132, Kluwer Academic Publishers, Netherlands (Mar. 2001).

Declaration Under 37 C.F.R. § 1.132 of Dr. Jorge F. Paniagua-Solis filed Nov. 2, 2009 for U.S. Appl. No. 10/565,885, § 371(c) date: Jan. 25, 2006.

Office Action mailed Jul. 31, 2009 for U.S. Appl. No. 10/565,885, § 371(c) date: Jan. 25, 2006.

Office Action mailed Apr. 1, 2010 for U.S. Appl. No. 10/565,885, § 371(c) date: Jan. 25, 2006.

Office Action mailed Dec. 1, 2010 for U.S. Appl. No. 10/565,885, § 371(c) date: Jan. 25, 2006.

Office Action mailed Jan. 31, 2011 for U.S. Appl. No. 12/326,387, filed Dec. 2, 2008.

COMPOSITIONS OF F(AB')₂ ANTIBODY FRAGMENTS

CROSS REFERENCE TO RELATED APPLICATIONS

This application is a divisional of U.S. application Ser. No. 12/326,687, filed Dec. 2, 2008, now U.S. Pat. No. 8,075,893, which is a divisional of U.S. application Ser. No. 10/690,639, filed Oct. 23, 2003, now U.S. Pat. No. 7,485,303, which is a divisional of U.S. application Ser. No. 09/798,076, filed Mar. 5, 2001, now U.S. Pat. No. 6,709,655. The disclosures of all the above-referenced applications are hereby incorporated by reference in their entireties.

BACKGROUND OF THE INVENTION

1. Field of the Invention

The present invention is directed to a pharmaceutical composition comprising F(ab')₂ antibody fragments that are preferably free from albumin and of whole antibodies and also substantially free of pyrogens, and an effective amount of a pharmaceutically acceptable carrier. It is also directed to a method for the preparation of a pharmaceutical composition comprising F(ab')₂ antibody fragments using serum or blood plasma of a mammal that has been previously immunized as a source of antibodies. The serum or blood plasma is digested with an enzyme, pepsin, followed by separation and purification until the pharmaceutical composition of F(ab')₂ fragments are free of albumin and complete antibodies, and substantially free of pyrogens.

2. Background Art

Antibodies are proteins of a globulin type known as immunoglobulins that are present in blood serum as a response of the immune system to the invasion of some foreign substance or organism, and are characterized for specifically combining with those substances that are foreign to the organism, neutralizing them and precipitating them so that they are removed from circulation. Various industrial applications have been developed with them for the diagnosis, monitoring, prevention and treatment of different ailments.

In regions where, due to climatic conditions, venomous animals abound, antibodies have been given a special use to combat venom. A large number of doses are applied when treating patients with scorpion, spider and snake stings or bites, principally. At present, a use that is gaining in importance is as a treatment for auto-immune diseases like rheumatoid arthritis, immune-dependent diabetes mellitus, AIDS, hemophilic anaemias, rheumatic fever, multiple sclerosis, thyroiditis and psoriasis, among others. In these cases, anti-cytokine antibodies are applied either directly to the patient or by treating blood that has been taken from and is subsequently re-fed to the patient, in order to remove the cytokines generated by the organism itself in response to the ailment. If such cytokines are not removed, they will cause extremely troublesome symptoms (see U.S. Pat. Nos. 5,888,511 and 4,940,670).

There are several kinds of immunoglobulins, known as IgG, IgM, IgD, IgA and IgE, of which IgGs are the most abundant in the blood circulation. IgGs correspond to a mature immune response and therefore include the vast majority of antibodies that are commercially produced. All the IgGs have the same general structure (which can be seen in FIG. 1). They are composed of four polypeptide chains, two that are heavy (H) and two light (L), which are joined together by disulfide bridges. The two heavy chains, in turn, are joined together by two other disulfide bridges known as the hinge region, approximately halfway along the chains. A little closer to the amino terminal region, each heavy chain is joined by a disulfide bridge with a light chain. Each heavy chain has three constant regions, $C_H1$, $C_H2$, and $C_H3$, the last two in the carboxy terminal region (before the hinge) and the first in the amino terminal region (immediately after the hinge) and a Variable region (VH) in the amino terminal end, while each light chain has only one constant region, CL, in the carboxy terminal end and one variable region, VL, in the amino terminal end.

When the IgG is digested enzymatically, different fragments are obtained depending on the enzyme used, that is, if papain is used, three fragments are obtained, the crystallizing fragment (Fc) and two antigen-binding fragments (Fab) and, if pepsin is used, one F(ab')₂ fragment is obtained, while the crystallizing fragment is digested. The foregoing is due to the fact that papain cuts the heavy chains immediately after the hinge (towards the amino terminal region), while pepsin cuts them before the hinge (towards the carboxy terminal region). Fab and F(ab')₂ fragments conserve their capacity to specifically bind to the antigen that gave rise to them. F(ab')₂ fragments also precipitate antigens, while the Fc antibody fraction normally acts as a marker signal for macrophages as well as the activation of lymphocytes for the recognition and phagocytosis of the antigen-antibody complex.

The Fc fragment comprises the antigenic determinants of the antibody in such a way that when a patient is administered whole antibodies generated in some animal of another species, the patient generates an immune response against these antigenic determinants. This may give rise to varied adverse secondary responses that can even include anaphylactic shock.

These problems are significantly reduced when the antibodies are previously digested with papain or pepsin and only the resulting purified Fab or F(ab')₂ fragments are administered.

The use of Fab or F(ab')₂ fragments has another advantage that is known as the concept of distribution volume, which is simply the volume of the body in which a determined drug is dissolved. This volume can refer to the circulating blood alone, as is the case of IgG, or can include a larger part of body water in the case of the fragments. For this reason, as Fab and F(ab')₂ have a greater corporeal volume they can neutralize toxins lodged in various tissues, not only in the blood. They can even cross the blood/brain barrier in both directions and be used to neutralize or eliminate neurotoxins.

The use of F(ab')₂ fragments has a particular advantage over the use of Fab fragments in that they are retained far longer in the organism because they have double the molecular weight. Moreover, they conserve their capacity to precipitate the antigen in physiological conditions as well as maintaining a size that allows them access to a distribution volume that is sufficient for treatment purposes.

Due to the fact that the F(ab')₂ fragments conserve the main characteristics of the antibodies, the applications of the antibodies extend to F(ab')₂ fragments, with the additional advantage that because they lack the Fc fragment, recognition as foreign by a patient to whom they are administered is less likely. This provides greater tolerance to application of F(ab')₂ fragments and reduces the possibility of secondary reactions, which is particularly useful for prolonged treatments such as those applied in autoimmune diseases.

It has been known for many years that soluble proteins (particularly serous proteins) lose solubility as the concentration of neutral salts (such as ammonium and sodium sulfates) in the solution increases. In this way, for example, euglobulin precipitates with 13.5% sodium sulfate, pseudoglobulin with 17.4% and pseudoglobulin 2 with 21.3%. This fact has been used to partially purify antibodies from serum or plasma.

Several approaches in the production of antibodies and their fragments have been reported in the literature. For example, U.S. Pat. No. 4,849,352, to Sullivan et al., claims the production of both Fab fragments through the digestion of antibodies with papain immobilized in polyacrylamide. Sullivan et al. also claims the production of $F(ab')_2$ fragments through the digestion of antibodies with immobilized pepsin, obtaining Fab and Fc or $F(ab')_2$ fragments and subsequently purifying the fragments through immunoaffinity, passing them through a polyacrylamide sieve containing the specific antigen of the antibodies in question. Later the Fab or $F(ab')_2$ fragments that have specifically bound to the molecules in the sieve are recovered with some strongly ionic solution. The use of immobilized enzymes for digestion and immobilized antigens for purification could prove to be extremely expensive for the large scale commercial production of preparations of antibody fragments, which is a drawback despite the purity of the fragments obtained.

Furthermore, although an antigenic sieve may be useful for producing antibody fragments against pure substances, this method is not economically feasible to produce antibodies against venoms that are mixtures of a large number of toxins, many of which have a biological effect.

Another approach is shown in U.S. Pat. No. 5,733,742 in which Landon claims a process to produce Fab fragments using whole blood in a sterile medium, in which the whole blood is put directly into contact with the enzyme, free or immobilized, that has preferably been purified. Subsequently, the cell residues are removed by centrifugation, separating and recovering the resulting fragments that are subsequently purified preferably by immunoaffinity. Again, Landon used purified antigens which, unlike venoms, can easily be bound to supports to obtain a sieve for the purification of the Fab of interest. Landon never used or discussed the method of obtaining Fab fragments against antigens that are mixtures of many substances, as is the case of venoms. He only worked with papain and chemopapain and did not discuss the possibility of using pepsin.

An additional approach to the production of Fab fragments is shown in U.S. Pat. No. 4,814,433 in which Fredrickson describes a procedure for obtaining papain free Fab. He observes that when antibodies are digested by this enzyme some contaminants remain in the solution. These contaminants are hybrid compounds of the papain joined by disulfide bridges to some of the fragments resulting from the digestion, which the papain can subsequently continue digesting and degrading the fragments obtained. In order to solve the problem, Fredrickson used antipapain antibodies, which capture the hybrid compound of the enzyme. Subsequently, the fragments were purified by passing the solution along a column with protein A in which the Fc fragments and the hybrid compounds were retained. This problem, present in the digestion with papain, has not been reported when digestion is done with pepsin.

Some traditional methods involve the digestion of pepsin and the precipitation of the fraction of the fragments with ammonium or sodium sulfates, but a pre-separation is usually done with the antibodies by precipitation with sulfate and then digestion of the antibody fraction. However, large losses have been reported of the biological activity in the resulting fragments and a high content of intact antibodies and other contaminants.

As can be seen from the background, although there are several methods for the production of Fab antibody fragments, they are often difficult to apply as immunogens in the case of complete venoms. Furthermore, the advantage of using $F(ab')_2$ fragments in this case is clear since they have a greater retention time than Fab and do precipitate neutralizing toxins. Moreover, the reports of $F(ab')_2$ fragment production by means of digestion with pepsin have given evidence of a considerable loss of biological activity and a high content of whole antibodies and other impurities, which has discouraged the commercial production of pharmaceutical products comprising this type of fragment.

BRIEF SUMMARY OF THE INVENTION

In one aspect, the invention relates to a pharmaceutical composition comprising $F(ab')_2$ antibody fragments that are preferably free from albumin and of whole antibodies and also substantially free of pyrogens.

Another aspect of the present invention is directed to a pharmaceutical composition comprising $F(ab')_2$ antibody fragments in an effective amount of a pharmaceutically acceptable carrier.

In still another aspect of the invention, the invention provides a pharmaceutical composition comprising $F(ab')_2$ antibody fragments which neutralizes or eliminates toxins in tissues and blood.

Another aspect of the invention relates to a pharmaceutical composition comprising $F(ab')_2$ antibody fragments which neutralizes a complex mixture of antigenic molecules such as the venom of venomous animal.

Another aspect of the present invention is directed to a method for the preparation of a pharmaceutical composition comprising $F(ab')_2$ antibody fragments using the serum or blood plasma of a mammal that has been previously immunized as a source of antibodies. The serum or blood plasma is digested with an enzyme, pepsin, followed by separation and purification until the pharmaceutical composition of $F(ab')_2$ fragments are free of albumin and complete antibodies, and substantially free of pyrogens.

Other aspects of the present invention will be apparent to one of ordinary skill on consideration of the present disclosure.

BRIEF DESCRIPTION OF THE DRAWINGS/FIGURES

FIG. 1 is a general structure of an Antibody. H represents a heavy chain. L represents a light chain, C represents a constant region whether in a heavy or in a light chain and V represents a variable region whether in a heavy or in a light chain. HiR represents the hinge region.

Figure 2:
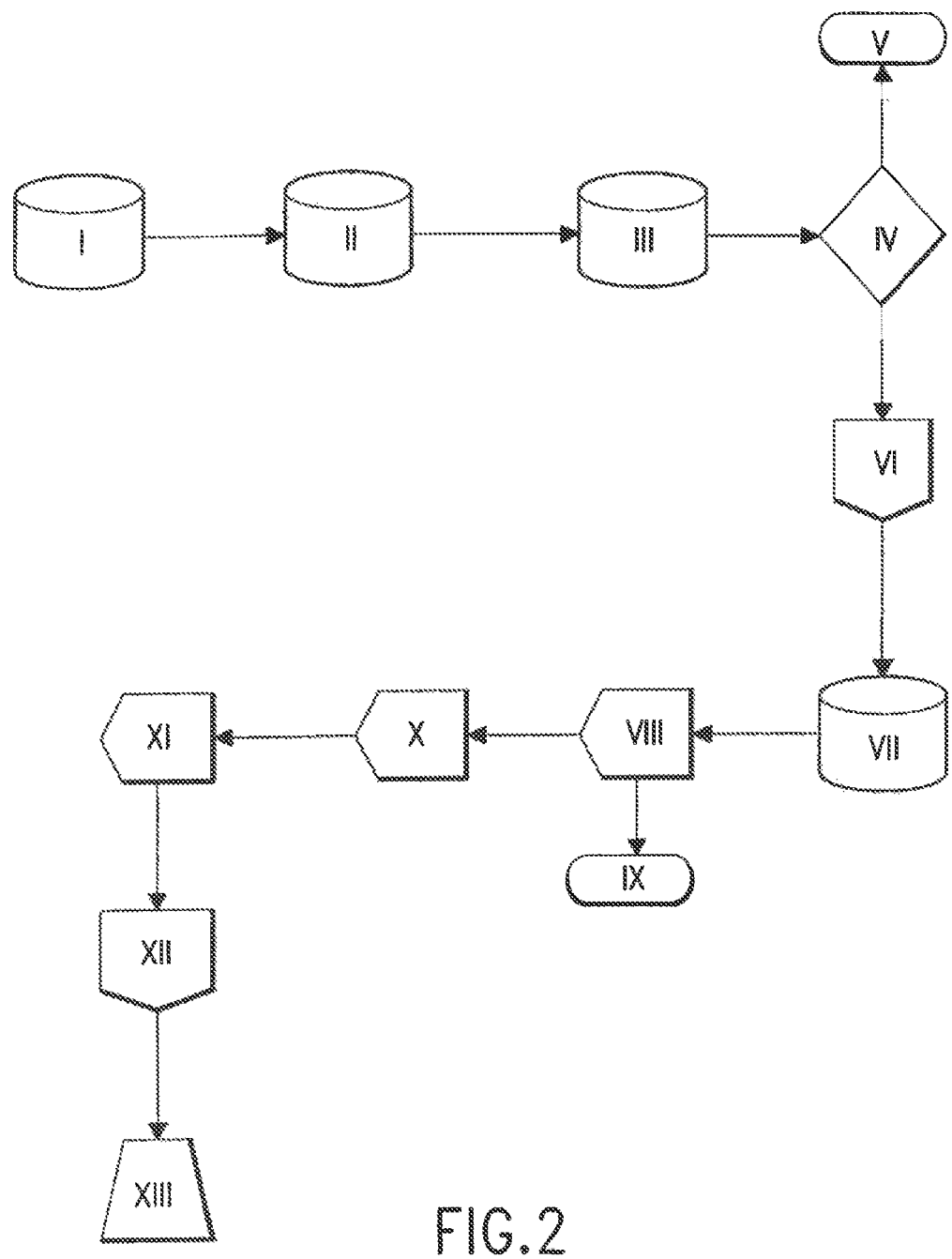

FIG. 2 is a diagram of $F(ab')_2$ production. The main stages of the process of the present invention for the production of $F(ab')_2$ fragments are outlined in the Figure. Blocks I to XII represent: Hyperimmune blood plasma mixture (I); Digestion of the plasma (II); Precipitation of undesired protein fragments (III); Clarification of the $F(ab')_2$ solution (N); Waste containing undesired protein fragments precipitate (V); partially purified $F(ab')_2$ solution (VI); precipitation of $F(ab')_2$ from solution (VII); Centrifugation (VIII); Waste containing low molecular components and salts (IX); Dialysis or ultrafiltration (X); sterile filtration and formulation (XI); Lyophilization (XII); Final product (XIII).

Figure 3:
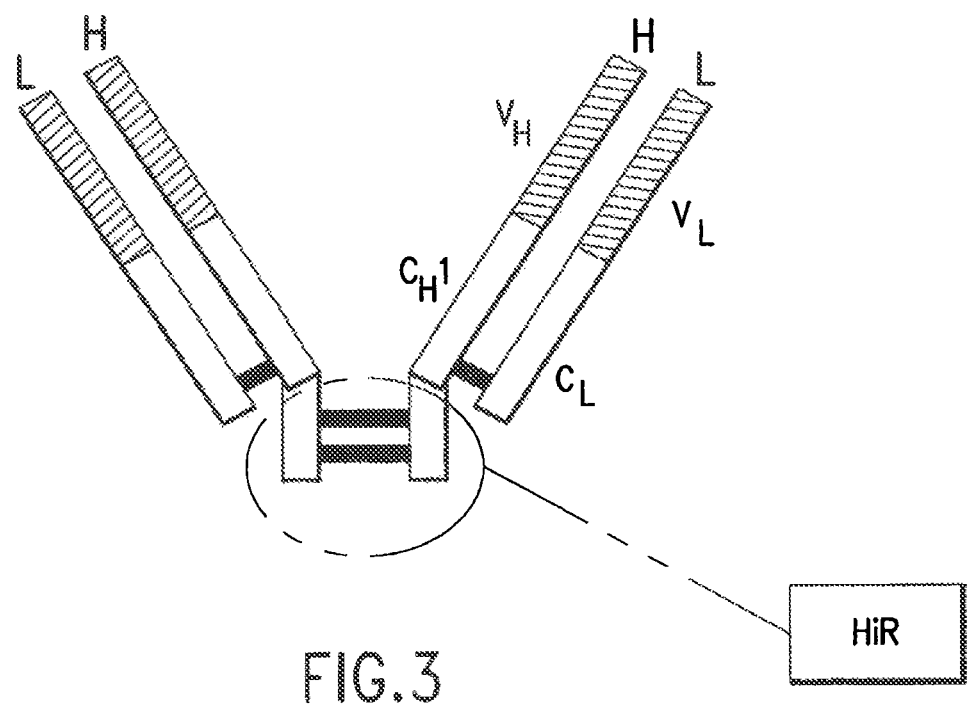

FIG. 3 is a general structure of an $F(ab')_2$ fragment. H represents a heavy chain fragment. L represents a light chain. C represents a constant region whether in a heavy chain fragment or in a light chain and V represents a variable region whether in a heavy chain fragment or in a light chain. HiR represents the hinge region.

Figure 4:
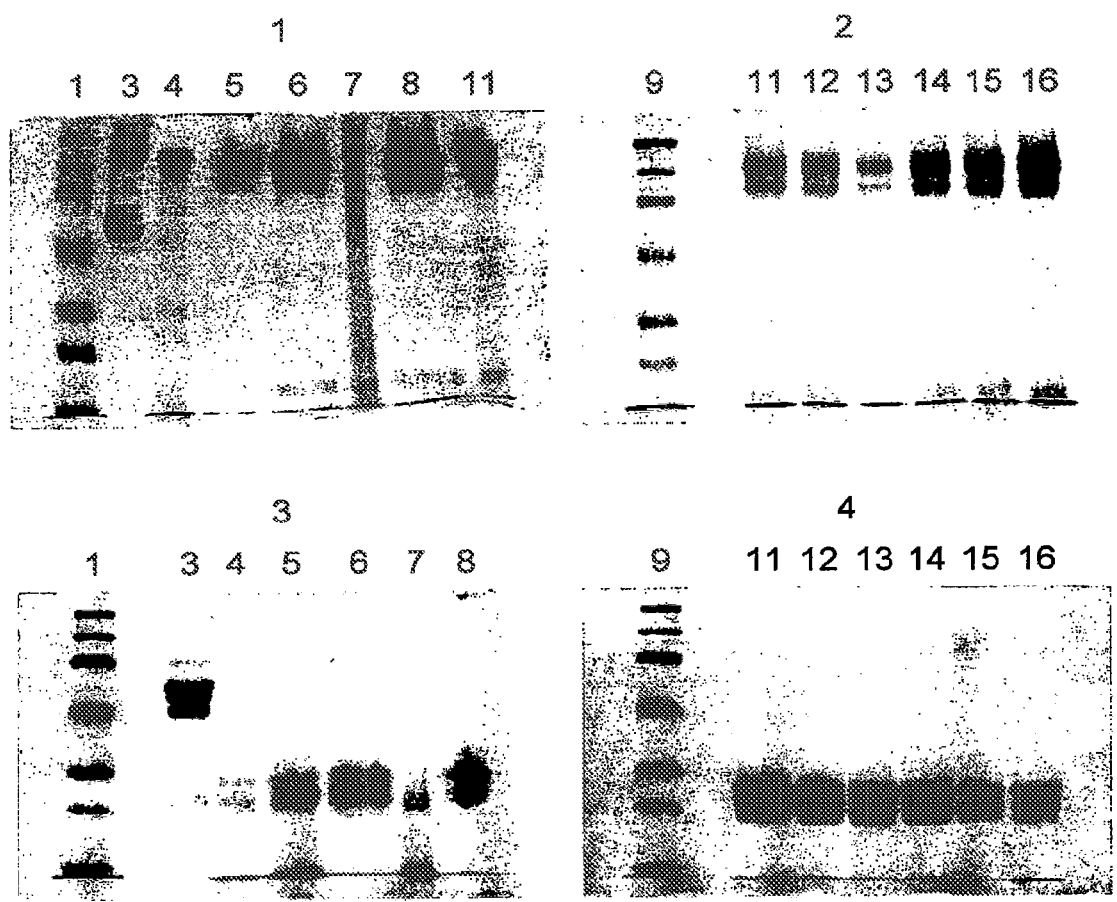

FIG. 4 is an electrophoresis of the different stages of the process for obtaining F(ab')$_2$ against polyvalent scorpion venom. Lanes 1 and 9 correspond to molecular weight markers: Myosin (205 Kd), R-galactosidase (121 Kd), Bovine serum albumin (70 Kd), Ovalbumin (52.4 Kd), Carbonic anhydrase (34.9 Kd), Soybean Trypsin Inhibitor (29.1 Kd), Lysozyme (20.7 Kd) and Aprotinin (6.9 Kd); Lanes 3 to 8 represent: Blood plasma, digested plasma, the mixture from the first precipitation, filtrate, waste and mixture from the second precipitation and Lanes 11 to 16 represent: precipitate paste, dialysis, waste, raw F(ab')$_2$ (Concentrated), Sterile formulated F(ab')$_2$ solution and Final product. Gels 1 and 2 are under non-reducing conditions and gels 3 and 4 are under reducing conditions.

Figure 5:
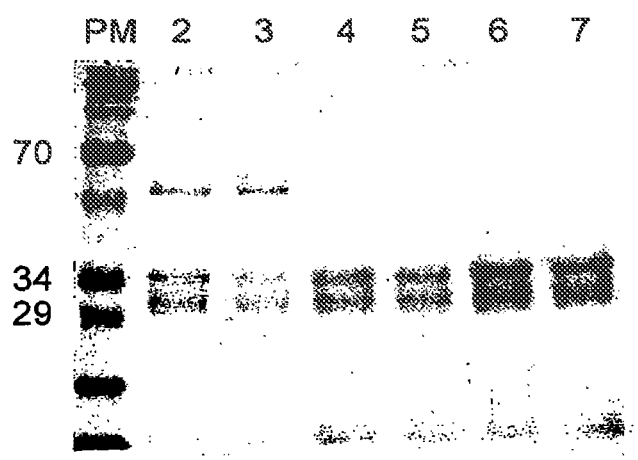

FIG. 5 is an electrophoresis of different lots of F(ab')$_2$ fragments against the venom of the black widow spider. Lane 1 corresponds to molecular weight markers: Myosin (205 Kd), β-galactosidase (121 Kd), Bovine serum albumin (70 Kd), Ovalbumin (52.4 Kd), Carbonic anhydrase (34.9 Kd), Soybean Trypsin Inhibitor (29.1 Kd), Lysozyme (20.7 Kd) and Aprotinin (6.9 Kd). Lanes 2-7 are different lots of F(ab')$_2$ fragments against the venom of the black widow spider.

Figure 6:
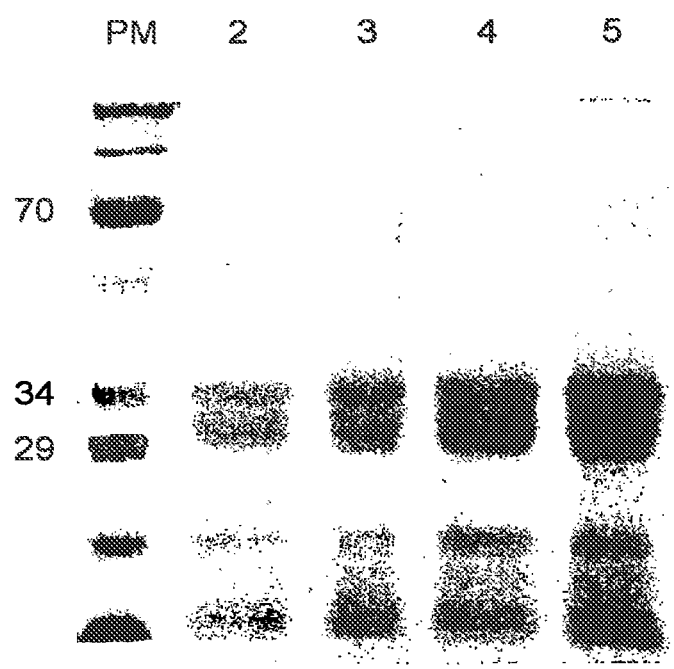

FIG. 6 is an electrophoresis of different lots of F(ab')$_2$ fragments against the venom of the coral snake. Lane 1 corresponds to molecular weight markers: Myosin (205 Kd), β-galactosidase (121 Kd), Bovine serum albumin (70 Kd), Ovalbumin (52.4 Kd), Carbonic anhydrase (34.9 Kd), Soybean Trypsin Inhibitor (29.1 Kd), Lysozyme (20.7 Kd) and Aprotinin (6.9 Kd). Lanes 2-5 are different lots of F(ab')$_2$ fragments against the venom of the coral snake.

Figure 7:
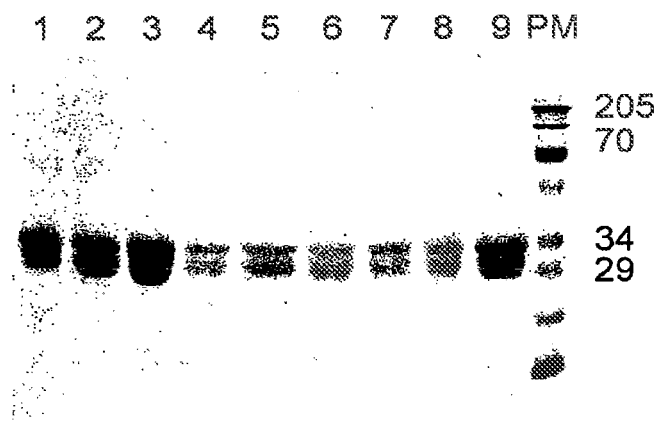

FIG. 7 is an electrophoresis of different lots of F(ab')$_2$ fragments against the venom of snakes of the *Bothrops, Crotalus* and *Lachesis* genera. Lanes 1-9 are different lots of F(ab')$_2$ fragments against the venom of snakes of the *Bothrops, Crotalus* and *Lachesis* genera; while lane 10 corresponds to molecular weight markers: Myosin (205 Kd), β-galactosidase (121 Kd), Bovine serum albumin (70 Kd), Ovalbumin (52.4 Kd), Carbonic anhydrase (34.9 Kd), Soybean Trypsin Inhibitor (29.1 Kd), Lysozyme (20.7 Kd) and Aprotinin (6.9 Kd).

Figure 8:
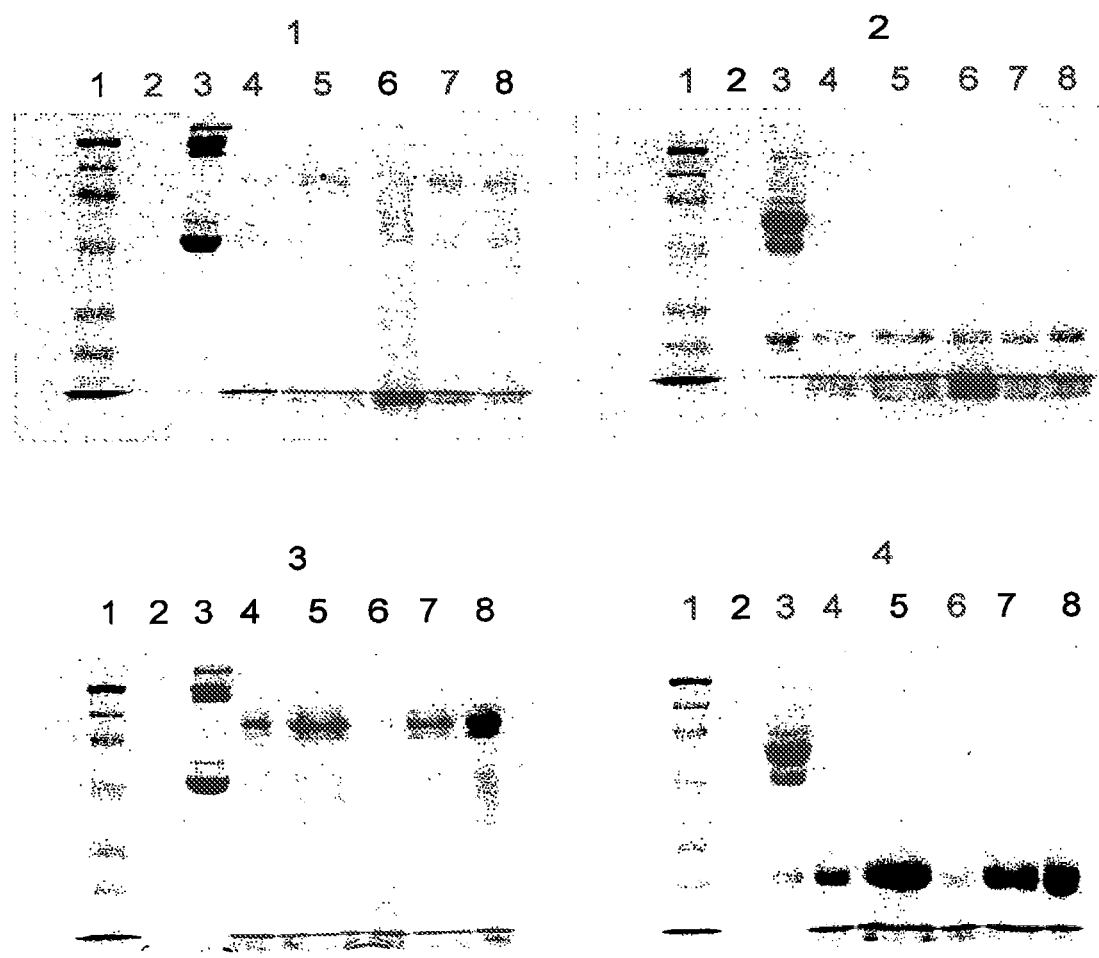

FIG. 8 is an electrophoresis of different stages of the process for obtaining F(ab')$_2$ against cytokines. Lane 1 corresponds to molecular weight markers: Myosin (205 Kd), β-galactosidase (121 Kd), Bovine serum albumin (70 Kd), Ovalbumin (52.4 Kd), Carbonic anhydrase (34.9 Kd), Trypsin Inhibitor (29.1 Kd), Lysozyme (20.7 Kd) and Aprotinin (6.9 Kd). Lane 2 is empty and Lanes 3 to 8 contain blood plasma, digested plasma, filtrate, filtrate waste, paste obtained from centrifugation and concentrate after dialysis. Gels 1 and 2 correspond to F(ab')$_2$ anti-TNF-α under non-reducing and reducing conditions. Gels 3 and 4 correspond to F(ab')$_2$ anti interferon-γ under non-reducing and reducing conditions.

DETAILED DESCRIPTION OF THE INVENTION

The following glossary is provided as an aid to understand certain terms herein. The explanation provided in the glossary are for illustrative purposes and do not limit the scope of the invention.

The term "substantially free" refers to the absence of pyrogen and protein material foreign to F(ab')$_2$ such as albumin or whole antibodies in accordance with the standards of the Mexican Pharmacopeia.

The term "aseptic conditions" refer to precautionary measures or methods employed in handling the different products from each step of the method of the present invention to prevent the contamination of culture or sterile media and infection by extraneous microorganisms.

The term "effective amount" or "pharmaceutically effective amount" of a compound in unit dose of the composition depends upon the number of factors. Included among these factors are quantity of the other ingredients when used and tolerance of the active ingredient of composition. Effective amount of the active ingredient ranges from about 8% to about 35% by weight based on the total weight of the composition. The amount of F(ab')$_2$ preparation to be filled in each flask varies depending upon the specie from which the venom was prepared. For compositions against scorpions, the F(ab')$_2$ preparation to be filled in each flask is the amount necessary to neutralize from about 135 to about 220 lethal doses 50% of the venom. For compositions against black widow spider, the amount necessary to neutralize is from about 540 to about 880 lethal doses 50% of the venom. For compositions against coral snake, the amount necessary to neutralize is from about 360 to about 660 lethal doses 50% of the venom. For compositions against *Bothrops* and *Crotalus*, the flasks are filled with the amount necessary to neutralize from about 700 to about 1100 lethal doses 50% of the venom.

By "pharmaceutically acceptable carrier" is meant solid or liquid filler, diluent or substance which may be safely used in systemic or topical administration. Depending on the particular route of administration, a variety of pharmaceutically acceptable carriers well known in the art include solid or liquid fillers, diluents, hydrotropes, surface active agents, and encapsulating substances. The amount of carrier employed in conjunction with the F(ab')$_2$ fragments is enough to provide a practical quantity of material per unit dose of composition.

Pharmaceutically acceptable carriers for systemic administration that may be incorporated in the composition of the invention include sugar, starches, cellulose, vegetable oils, buffers, polyols and alginic acid. Specific pharmaceutically acceptable carriers are described in the following documents, all incorporated herein by reference: U.S. Pat. No. 4,401,663 to Buckwalter et al., issued Aug. 30, 1983; European Patent Application No. 089710, LaHann et al., published Sep. 28, 1983; and European Patent Application No. 0068592, Buckwalter et al., published Jan. 5, 1983. Preferred carriers for parenteral administration include propylene glycol, pyrrolidone, ethyl oleate, aqueous ethanol, and combinations thereof.

Representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologs, polyethylene glycol, polyvinyl alcohol, polyacrylamide, sodium lauryl sulfate, poly (ethylene oxide), polyvinylpyrrolidone, glycol monostearate, propylene glycol monostearate, xanthan gum, tragacanth, sorbitan esters, stearyl alcohol, starch and its modifications. Suitable ranges vary from about 0.5% to about 1%.

In accordance with the above, the present invention is related to a pharmaceutical composition that comprises F(ab')$_2$ antibody fragments that are free of albumin and whole antibodies and substantially free of pyrogens. The antibodies from which the fragments are obtained can be generated against purified molecules, i.e., free of other antigenic molecules. Examples of purified molecules include cytokines, particularly TNF-α and interferon-γ or other pharmaceutical drugs and the like. The antibodies from which the fragments are obtained can also be generated against complex mixtures of immunogenic molecules such as the venoms of poisonous animals that are complex mixtures of peptides and toxins, and even a mixture of the venoms of several species. More particularly, the pharmaceutical composition of the present invention has been successfully obtained using antibodies generated against the cytokines TNF-α and interferon-γ, against the total venom of the black widow spider (*Latrodectus mactans*), the total venom of the coral snake (*Micrurus nigroscinctus*), against the venoms of snakes of the genera *Bothrops, Crotalus, Agkistrodon, Lachesis* and *Sistrurus* and against a mixture of venoms (polyvalent venom) of scorpions, particularly *Centruroides noxius, C. limpidus limpidus, C. limpidus tecomanus* and *C. suffusus suffusus*. The pharmaceutical composition of the present invention comprises F(ab')$_2$ fragments, the general structure of which is presented in FIG. 3, that lack the Fc region, are free of albumin and complete antibodies, and lack antigenic determinants that would make the patient's organism recognize them as foreign. In this way, the pharmaceutical composition of this invention can be administered on more than one occasion, dramatically reducing the possibility of a secondary response. The administration is normally systemic administration, whether intramuscular or intravenous. The amount varies on the characteristics of the subject to be administered, the specie that bit or stung the subject, and the degree of administration. For example, for scorpions or black widow spiders, about 1 to about 3 flasks are employed while about 1 to about 10 flasks are used for snakes.

Similarly, this invention is aimed at a method for the production of F(ab')$_2$ antibody fragments, substantially free of albumin, whole antibodies and pyrogens from a source of antibodies such as serum, plasma or the blood of some animal which has been subjected to an immunization scheme with an immunogen, stimulating the generation of specific antibodies against the immunogen.

Obtaining a source of antibodies of a good quality, that is with a high titer of antibodies with high specificity against the immunogen and a high degree of representation of the possible different antibodies that can recognize the various antigenic determinants of the immunogen, is beneficial to obtain F(ab')$_2$ antibody fragments substantially free of pyrogens and protein material foreign to said fragments.

The initial material, that is the antibody source, should preferably come from several animals in order to have a greater universe of different specific antibodies against the different epitopes of the immunogen. The antibody source can be blood, serum or preferably plasma.

With the purpose of obtaining a product substantially free of pyrogens, extremely rigorous conditions of asepsis must be maintained during the whole process, although it is not necessary to have a closed sterile system during the whole process as established by Landon in U.S. Pat. No. 5,733,742.

The first step in the method is the digestion of the protein material contained in the antibody source, although dilution of the antibody source is recommended as an option, especially in the case of plasma. To do so, the pH is lowered to about 3.2±0.2 and sufficient amounts of the enzyme pepsin (from about 0.5 to 1 g/l depending on the enzyme activity) are added. This mixture is incubated with agitation for the intervals of time needed to obtain a high degree of hydrolysis (close to 100% of the hydrolyzed antibodies) at a temperature of nearly 20° C.

Precipitation is then conducted by adding ammonium sulfate in a proportion of between about 16 and about 22% (W/V), preferably about 21%, incubating the mixture for at least 30 minutes at a temperature of about 55±about 4° C. The mixture is subsequently cooled and left to settle at a temperature of between about 8 and about 12° C. for at least 2 hours. This settling period is of great importance in the formation of particles of a larger size, which results in greater precipitation efficiency, and the absorption of other impurities of a lesser size that would not precipitate otherwise. In this step, most of the undigested serum proteins such as albumin and fibrinogen and the large fragments resulting from theft digestion are precipitated, while the F(ab')$_2$ fragments resulting from the digestion of the antibodies remain in the solution.

The following step comprises clarifying the solution by eliminating the smallest particles formed during the precipitation. To do so, the use of 12, 8 and 4, and optionally 0.22µ, tray filters is suggested to reduce the possible presence of pyrogens. F(ab')$_2$ fragments and some soluble peptides produced by the degradation of the albumin and fibrinogen can be found in the recovered supernatant.

The supernatant from the foregoing step is submitted to a further precipitation by adding ammonium sulfate in a proportion between about 32 and 38%, preferably about 35% Weight/Volume at a pH of about 6.8±0.5. Again, it is important to allow for the longest settling period possible, in refrigeration, ideally for at least 12 hours, with which larger particles with greater precipitation efficiency are obtained. The salts and some components of a low molecular weight that do not precipitate in the conditions handled in the previous steps remain in soluble form in the supernatant.

In order to separate the particles from the supernatant, it is recommended to centrifuge the suspension formed at between about 10,000 and 15,000 rpm, recovering a paste of precipitated F(ab')$_2$ fragments.

With the purpose of purifying the produced, isolated F(ab')$_2$ fragments, it is necessary to remove the salts and components of a low molecular weight that have been captured in the precipitation. To do so, the crystal paste can be submitted to dialysis or alternatively to ultrafiltration. In both cases, the membrane pore must have a size that permits the salts and components of a low molecular weight to pass through it, but not the F(ab')$_2$ fragments, which become soluble again as the concentration of salts decreases.

In order to guarantee that the final product is substantially free from pyrogens, the solution formed in the previous step is passed through a sterile filter and is subsequently formulated with pharmaceutically acceptable excipients for injectable substances. Polyvinylpyrrolidone, mannitol or dextrose may be used, Osmolytes (such as glycerol), stabilizers like saccharose, and some salts like NaCl may be used in order to achieve isotony in the solution to be administered, dosifying the product so that each dose (flask) contains adequate potency.

The product is subsequently lyophilized and the flasks containing it are hermetically sealed. In this way, an easily soluble product is obtained (the content of one flask in 5 ml in less than 1 minute), which is substantially free of pyrogens according to the Pharmacopoeia and protein material foreign to F(ab')$_2$ (0% albumin, 0% whole antibodies).

Methodology

Pyrogen Test

The test was conducted in accordance with the Pharmacopoeia of Mexico MGA 0711 Pyrogen Test.

Biological Potency Assay

The assay was conducted in accordance with the Pharmacopoeia of Mexico MPB

050. Anti-poison sera potency.

Electrophoresis SDS

Electrophoresis was conducted using 10% acrylamide gels, in both reducing and non-reducing conditions. The protein concentration in each sample was standardized at 18 µg per lane. They were developed with ethidium bromide.

Solubility

Solubility was conducted by adding 5 ml of bidistilled water to each flask and shaking vigorously and observing the solubility of the content of the flask after less than one minute against the light.

Lethal Doses 50% determination.

To determine the lethal doses 50% for every venom disclosed, eight serial dilutions (1:3) of every venom in saline solution were prepared. After that, eight groups of 5 mice (Balb/c) of an average weight of 15 g were injected intraperitoneally with 100 µg of the dilutions, one group for each dilution of each venom. Mortality of mice was read after 24 hours.

Experimental data of percentage of mortality vs. logarithm of venom doses were adjusted by a non-lineal regression with GraphPad PRISM software (GraphPad Software Inc., San Diego, Calif.) and the Lethal Doses 50% (LD50) were calculated for each venom as the dose at which 50% of the mice administered with such dose died.

ELISA Procedure for the Determination of Anti-Venom Titer.

1. The lyophilized venoms were reconstituted in 0.1M sodium carbonate buffer pH 9.5 to a concentration of 5 µg/ml.
2. 96 wells ELISA plates were coated by adding 100 µl of venom per well and incubated overnight at 4° C.
3. Wells were washed three times with 200 µl/well of washing solution (50 mM Tris/HCl pH 8, 0.150 mM NaCl, 0.05% Tween 20).
4. Unspecific unions were blocked with blocking solution (50 mM Tris/HCl pH 8.0, 0.5% gelatin, 0.2% Tween 20) for 2 hours at room temperature.
5. Serial dilutions of antivenom with an initial stock of 1:10 were made in situ reaction buffer (50 mM Tris/HCl pH 8.0, 500 mM NaCl, 0.1 mg/ml gelatin, 0.05% Tween 20)
6. Thus, 100 µl of reaction solution (dilutions) were added to each well and 50 µl of the antivenom solution were mixed and then 50 µl of the dilution were transferred to the next well and so on until 10 wells, and were incubated 1 hour at room temperature.
7. Again, wells were washed three times with 200 µl/well of washing solution.
8. A second antibody against horse was added, which was conjugated to the enzyme peroxidase diluted 1:2500 in reaction buffer and was incubated at room temperature for 1 hour.
9. Reaction was developed by adding 100 µl/well of the chromogenic substrate ABTS and incubating for 10 minutes at room temperature.
10. Reaction was stopped by adding 25 µl/well of concentrated fluorhydric acid.
11. Absorbance was read at 405 nm with an ELISA reader

EXAMPLES

In order to illustrate better the pharmaceutical compositions and the method of the present invention for the production of F(ab')$_2$ antibody fragments, the following specific examples are provided to better assist the reader in the various aspects of practicing the present invention. As these specific examples are merely illustrative, nothing in the following descriptions should be construed as limiting the invention in any way.

Example 1

Development of an Adequate Source of Antibodies

In order to have an adequate source of antibodies, it is necessary to attempt to have the following requisites: a) high titer antibodies, implying a high concentration of antibodies and a high percentage of said antibodies that are specific against the antigen in question and a population of wide spectrum antibodies, that is, against the different epitopes of each of the molecules comprising the antigen; this is particularly important in the case of venoms.

In order to obtain a high titer it is necessary to follow the following recommendations:

Adequately prepare and formulate (conjugations, use of aids) antigens to maximize their immunogenic capacity.

Apply immunization schemes capable of efficiently activating the animal's immune system.

Determine in each group of animals the moment when they reach each stage of the immune response curve (where they reach a peak and level off, mainly). This can be performed by means of neutralization assays.

Maintain a selection of high producer animals taking special care to prolong their average life span with respect to antibody production.

In order to obtain a population of wide spectrum antibodies, it is recommended to use a mixture of blood, plasma or serum from different animals.

Immunization schemes like those recommended in the literature were followed with doses of venoms that ranged from 3 to 150 $DL_{50}$ per horse throughout 12 immunizations given over 5 to 6 weeks for the base schemes, and from 70 to 450 $DL_{50}$ per horse throughout 5 immunizations over 3 weeks for the reinforcement schemes, according to the type of venom applied. Freund's Complete and Incomplete adjuvants were used as well as a saline isotonic solution, using a total of 5, 10 or 20 ml in the different inoculations.

The antibody source used in the present invention was obtained from bleeding animals, at a rate of 6 to 10 liters per horse per bloodletting, two bloodlettings during the 15 days following the last inoculation of each scheme.

The antibody source for the method of the present invention can be a mixture of blood from different animals immunized with the same antigen, or the serum produced by its coagulation, or preferably the plasma resulting from the separation of the cell packet by sedimentation. The particular use of plasma has the advantage in large scale production that the cell packet can be washed and suspended in a physiological solution and fed back to the animal from which it was obtained, thus reducing the stress associated with the drop in blood cells and producing the smallest impact possible on antibody production.

In this way, antibody sources were produced against the venom of the scorpion (a polyvalent venom which is a mixture of the venoms of the scorpions *Centruroides noxius, C. limpidus limpidus, C. limpidus tecomanus* and *C. suffusus suffusus*; of the black widow spider (*Lactrodectus mactans*); the coral snakes (*Micrurus nigroscienctus*); and snakes of the genera *Bothrop, Crotalus* and *Lachesis*, particularly the rattlesnake (*Crotalus durissus durissus*), the mute rattlesnake (*Lachesis muta stenophry*) and the nauyaca (*Bothrops asper*).

Example 2

Application of the Method of the Present Invention for the Production of Polyvalent Anti-Venom Against Scorpion Venom An antibody source was obtained as mentioned in Example 1, using in this case polyvalent scorpion venom (*Centruroides noxius, C. limpidus limpidus, C. limpidus tecomanus* and *C. suffusus suffusus*) as antigen, obtaining blood plasma as antibody source. The plasma of different animals immunized against the same polyvalent venom was mixed together.

The plasma was diluted with depyrogenized water 1:2 (inverse osmosis, sterilized and filtered by 0.22µ and the pH adjusted at about 3.2. Pepsin (filtered by 0.22µ) was added for digestion until nearly 390,000 units per liter were obtained and the mixture was left to react at a temperature close to 20° C. for about one hour, with agitation at about 15 minute intervals.

Once the reaction was completed, the mixture was heated to about 54° C. and ammonium sulfate was added in a proportion of 21% (weight/volume) and it was left to settle for 30 minutes. The mixture was subsequently refrigerated at a temperature of between about 4 and about 8° C. for a space of about 2 hours (although it can be stored for up to about 24 hours). The supernatant was recovered through decantation and clarified by passing it through tray filters of 12, 8 and 4µ.

Ammonium sulfate was again added to the clarified supernatant in a proportion of 35% (weight/volume), having previously adjusted the pH at about 6.8. It was left to settle for 12 hours. The mixture was subsequently centrifuged at some 15,000 rpm in a Sharples type centrifuge. The recovered paste contains F(ab')$_2$ fragments. The paste was submitted to a process of dialysis in cellophane, at between about 4 and about 12° C. for about 8 to 10 days. The resulting solution contained F(ab')$_2$ fragments specific against scorpion venom that is substantially pure and free of pyrogen.

Subsequently, the soluble part of that fraction that did not solubilize was separated and formulated by adding saccharose, NaCl, and glycerol, adjusting the pH at around 6.8 and it was dosified according to the determined potency in pyrogen free flasks that will then be lyophilized.

Tests for purity were conducted by Electrophoresis of different stages of the process and HPLC with the results shown in FIG. 4. It can clearly be seen that the F(ab')$_2$ fragments produced have a molecular weight of approximately 100,000 to 110,000 daltons (non-reducing conditions), while under reducing conditions, they are present as bands of 25,000 to 30,000 daltons. Similarly, potency tests were conducted showing that the pharmaceutical composition of the F(ab')$_2$ fragments thus obtained effectively neutralize scorpion polyvalent venom. The content of all the flasks sampled were soluble in 5 ml of bidistilled water in less than 1 minute.

Example 3

Application of the Method of the Present Invention for the Production of Anti-Venom Against the Venom of the Black Widow Spider A source of antibodies as described in Example I was then obtained, using the venom of the black widow spider (*L. Mactans*) and plasma was chosen as antibody source. The plasma obtained was processed in the same way as in Example 2.

FIG. 5 shows the electrophoresis gel in different stages of the process where it can be clearly seen that the F(ab')$_2$ fragments produced have a molecular weight of approximately 100,000 to 110,000 daltons (non-reducing conditions), while under reducing conditions, they are present as bands of 25,000 to 30,000 daltons. The potency test showed that the pharmaceutical composition comprising the F(ab')$_2$ fragments thus obtained effectively neutralizes the venom of the black widow spider. The contents of all the flasks sampled was soluble in 5 ml of bidistilled water in less than 1 minute.

Example 4

Application of the Method of the Present Invention for the Production of Antivenom Against the Venom of the Coral Snake A source of antibodies as described in Example 1 was then obtained, using the venom of the coral snake (*M. nigroscienctus*) and plasma was chosen as antibody source. The plasma obtained was processed in the same way as in Example 2.

FIG. 6 shows the electrophoresis gel in different stages of the process where it can be clearly seen that the F(ab')$_2$ fragments produced have a molecular weight of approximately 100,000 to 110,000 daltons (non-reducing conditions), while under reducing conditions, they are present as bands of 25,000 to 30,000 daltons. The potency test showed that the pharmaceutical composition comprising the F(ab')$_2$ fragments thus obtained effectively neutralizes the venom of the coral snake. The contents of all the flasks sampled was soluble in 5 ml of bidistilled water in less than 1 min.

Example 5

Application of the Method of the Present Invention for the Production of Anti-Venom Against the Venom of Snakes of the *Bothrops, Crotalus, Agkistrodon, Lachesis* and *Sistrurus* Genera A source of antibodies as described in Example 1 was then obtained, immunizing groups of animals separately with venom of snakes from each of the following genera: *Bothrops, Crotalus, Agkistrodon, Lachesis* and *Sistrurus*, one group for each venom, and plasma was chosen as antibody source. The plasma obtained for each of the snake venoms of the different genera was processed in the same way as in Example 2.

The F(ab')$_2$ obtained for each of the snake venoms of the different genera is mixed, considering putting the same proportion in terms of potency for each of them, before being formulated and dosified in flasks. Subsequently, they are formulated with suitable excipients and dosified and lyophilized in flasks.

FIG. 7 shows the electrophoresis gel in different stages of the process where it can be clearly seen that the F(ab')$_2$ fragments produced have a molecular weight of approximately 100,000 to 110,000 daltons (non-reducing conditions), while under reducing conditions, they are present as bands of 25,000 to 30,000 daltons. The potency test was conducted in the individual F(ab')$_2$ for each type of venom against the respective venom and subsequently in the mixture of F(ab')$_2$ against each type of venom separately, showing that the pharmaceutical composition comprising the F(ab')$_2$ fragments thus obtained effectively neutralizes the venom of snakes of any of the genera *Bothrops, Crotalus, Agkistrodon, Lachesis* or *Sistrurus*. The contents of all the flasks sampled was soluble in 5 ml of bidistilled water in less than 1 minute.

Example 6

Application of the Method of the Present Invention for the Production of Anti-Cytokines Using blood plasma obtained from goats immunized with a cytokine (both α-TNF and interferon-γ, separately) as source of antibodies, the same procedures were followed as in Example 2.

FIG. 8 shows the electrophoresis gels in different stages of the process where it can be clearly seen that the F(ab')$_2$ fragments produced have a molecular weight of approximately 100,000 to 110,000 daltons (non-reducing conditions), while under reducing conditions, they are present as bands of 25,000 to 30,000 daltons. The potency test showed that the pharmaceutical composition comprising the $F(ab')_2$ fragments thus obtained effectively neutralizes the TNF-α and interferon-γ cytokines, respectively. The contents of all the flasks sampled was soluble in 5 ml of bidistilled water in less than 1 minute.

Example 7

Crossed Immunological Reactions of the Composition of $F(ab')_2$ Against *Bothrops asper* and *Crotalus durissus durissus* (Antiviperin Composition) with the Venom of Other Species and Genera For each of the below mentioned snakes species, eight different amounts of the antiviperin composition together with a fixed amount of venom (equivalent to 5 $LD_{50}$) and saline solution to fix the volume, were incubated for 1 hr at 37° C. After that, eight groups of 5 mice (Balb/c) of an average weight of 15 g were injected intra peritoneally with a fixed volume of 700 µl, one group for each amount of the antiviperin composition. Mortality of mice was read after 24 hours.

Experimental data of percentage of mortality vs. logarithm of volume added (of the antiviperin composition) were adjusted by a non-lineal regression with GraphPad PRISM software (GraphPad Software Inc., San Diego, Calif.) and the Effective Doses 50% (ED50) (defined as the antivenom/venom proportion in which the lethal activity is reduced to 50% compared to the effect of the same amount of venom alone) were calculated for the antiviperin composition (antivenom) against each of the venoms. Table I shows the for the antiviperin composition against eight snakes species from 4 different species/three different genera.

TABLE 1

Effective Doses 50% ($ED_{50}$) expressed as milligrams (mg), for 5 lethal doses 50% ($LD_{50}$) of the venom from different snake species.

| Venom (5.0 $LD_{50}$) from: | $ED_{50}$ of the antiviperin composition (mg) |
| --- | --- |
| Bothrops alternatus | 5.88 |
| Bothrops neuwedii | 1.62 |
| Bothrops jararaca | 2.09 |
| Bothrops moojeni | 0.98 |
| Agkistrodon bilineatus | 4.39 |
| Bothrops asper | 0.61 |
| Crotalus durissus durissus | 1.73 |
| Bothrops nummifer | 7.05 |

The above results show that the antiviperin composition containing at least two $F(ab')_2$ against *Bothrops* and *Crotalus* genera neutralizes species from genera *Bothrops*, *Crotalus* and *Agkistrodon*.

Example 8

Determination of Antiviperin Composition Titer Against 16 Snakes Species by ELISA ELISA plates were prepared with venom from 16 snake species, reacted with the antiviperin composition (against venom from *Bothrops* and *Crotalus* genera), developed and read at 405 nm. Experimental data for Absorbance at 405 nm vs. logarithm of dilution factor (of the antiviperin composition) were adjusted by a non-lineal regression with GraphPad PRISM software (Graphpad Software Inc., San Diego, Calif.) and the Titer (defined as the dilution factor at which half of the maximum response is reached) for the antiviperin composition against each venom were calculated and are represented in Table 2.

TABLE 2

Antiviperin composition titer against several snakes species from four different genera.

| Snake specie | Titer |
| --- | --- |
| Bothrops atrox asper | 2177 |
| Bothrops asper | 2842 |
| Bothrops nummifer | 890 |
| Bothrops undulates | 1802 |
| Crotalus basiliscus | 3073 |
| Crotalus durissus durissus | 1226 |
| Agkistrodon bilineatus bilineatus | 1120 |
| Crotalus scutulatus | 2884 |
| Bothrops alternates | 1774 |
| Bothrops neuwiedii | 3052 |
| Bothrops moojeni | 2230 |
| Bothrops jararaca | 2572 |
| Bothrops jararacussu | 2916 |
| Bothrops ammodytoides | 1438 |
| Crotalus durissus terrificus | 1040 |
| Lachesis muta stenophry | 2183 |

The results demonstrate that $F(ab')_2$ contained in the antiviperin composition of the present invention neutralizes venoms from snakes from the genera *Bothrops*, *Crotalus*, *Lachesis* and *Agkistrodon*.

The above examples have been depicted solely for the purpose of exemplification and are not intended to restrict the scope or embodiments of the invention. The invention is further illustrated with reference to the claims which follow hereto.

What is claimed is:

1. A composition comprising $F(ab')_2$ antibody fragments substantially free from albumin and whole antibodies and substantially free of pyrogens, wherein the composition binds to a purified antigenic molecule or a mixture of antigenic molecules found in spider venom, and wherein the $F(ab')_2$ antibody fragments are obtained by a method which comprises:
   (a) contacting a source of antibodies with pepsin under conditions to prepare an antibody digest containing $F(ab')_2$ antibody fragments, wherein the antibody digest is substantially free of unhydrolyzed antibodies; and
   (b) treating the antibody digest with two steps of ammonium sulfate precipitation, (i) one step at about 16% to about 22% weight by volume of ammonium sulfate, and (ii) another step at about 32% to about 38% weight by volume of ammonium sulfate, to thereby obtain a suspension containing $F(ab')_2$ antibody fragments substantially free of whole antibodies.

2. The composition of claim 1, further comprising a pharmaceutically acceptable carrier.

3. The composition of claim 1, wherein the composition is substantially free of viral particles.

4. The composition of claim 1, wherein the spider venom is from a spider of the genus *Latrodectus*.

5. The composition of claim 4, wherein the spider venom is from a black widow spider (*Latrodectus mactans*).

6. The composition of claim 1, wherein the method further comprises generating a source of antibodies from an animal that has been immunized with a mixture of antigenic molecules found in the spider venom prior to the contacting.

7. The composition of claim 1, wherein the F(ab')$_2$ antibody fragments are polyclonal F(ab')$_2$ antibody fragments.

8. The composition of claim 1, wherein the composition neutralizes a purified antigenic molecule or a mixture of antigenic molecules found in the spider venom.

9. A composition comprising F(ab')$_2$ antibody fragments substantially free from albumin and whole antibodies and substantially free of pyrogens, wherein the composition binds to a purified antigenic molecule or a mixture of antigenic molecules found in spider venom, and wherein the F(ab')$_2$ antibody fragments are obtained by a method which comprises:
   (a) generating a source of antibodies from an animal that has been immunized with a mixture of antigenic molecules found in spider venom;
   (b) contacting the source of antibodies with pepsin under conditions to prepare an antibody digest containing F(ab')$_2$ antibody fragments, wherein the antibody digest is substantially free of unhydrolyzed antibodies;
   (c) treating the antibody digest with two steps of ammonium sulfate precipitation, (i) one step at about 16% to about 22% weight by volume of ammonium sulfate, and (ii) another step at about 32% to about 38% weight by volume of ammonium sulfate, to thereby obtain a suspension containing F(ab')$_2$ antibody fragments substantially free of whole antibodies;
   (d) centrifuging the suspension to produce a composition comprising a paste of F(ab')$_2$ antibody fragments and a supernatant; and
   (e) removing the supernatant from the composition of (d).

10. The composition of claim 9, further comprising a pharmaceutically acceptable carrier.

11. The composition of claim 9, wherein the composition is substantially free of viral particles.

12. The composition of claim 9, wherein the spider venom is from a spider of the genus *Latrodectus*.

13. The composition of claim 12, wherein the spider venom is from a black widow spider (*Latrodectus mactans*).

14. The composition of claim 9, wherein the F(ab')$_2$ antibody fragments are polyclonal F(ab')$_2$ antibody fragments.

15. The composition of claim 9, wherein the composition neutralizes a purified antigenic molecule or a mixture of antigenic molecules found in spider venom.

* * * * *